United States Patent
D'Aversa et al.

(10) Patent No.: US 8,470,753 B2
(45) Date of Patent: Jun. 25, 2013

(54) PERSONAL CLEANSING SYSTEMS EXHIBITING LOW EYE IRRITATION POTENTIAL

(75) Inventors: Eugene D'Aversa, University Park, IL (US); Frank Wayne Wagner, University Park, IL (US)

(73) Assignee: Rhodia Operations, Aubervillers (FR)

( * ) Notice: Subject to any disclaimer, the term of this patent is extended or adjusted under 35 U.S.C. 154(b) by 0 days.

(21) Appl. No.: 13/356,723

(22) Filed: Jan. 24, 2012

(65) Prior Publication Data
US 2012/0196783 A1    Aug. 2, 2012

Related U.S. Application Data

(60) Provisional application No. 61/437,110, filed on Jan. 28, 2011.

(51) Int. Cl.
*A61K 8/00*    (2006.01)

(52) U.S. Cl.
USPC ............ 510/123; 510/124; 510/127; 510/130

(58) Field of Classification Search
None
See application file for complete search history.

(56) References Cited

U.S. PATENT DOCUMENTS

| | | | |
|---|---|---|---|
| 3,950,417 A | 4/1976 | Verdicchio et al. | |
| 4,110,263 A | 8/1978 | Lindemann et al. | |
| 4,138,371 A | 2/1979 | Verdicchio et al. | |
| 4,186,113 A | 1/1980 | Verdicchio et al. | |
| 4,426,310 A | 1/1984 | Verunica | |
| 4,443,362 A | 4/1984 | Guth et al. | |
| 4,726,915 A | 2/1988 | Verdicchio | |
| 4,849,127 A * | 7/1989 | Maxon | 510/537 |
| 4,992,266 A | 2/1991 | Knoll | |
| 5,478,490 A * | 12/1995 | Russo et al. | 510/122 |
| 7,417,020 B2 | 8/2008 | Fevola et al. | |
| 7,754,666 B2 | 7/2010 | Walters et al. | |
| 7,754,667 B2 | 7/2010 | Walters et al. | |
| 7,803,403 B2 | 9/2010 | Librizzi et al. | |
| 2002/0103092 A1* | 8/2002 | Tashjian et al. | 510/130 |
| 2002/0151446 A1 | 10/2002 | Piterski et al. | |
| 2005/0037040 A1 | 2/2005 | Arkin et al. | |
| 2005/0075256 A1 | 4/2005 | Librizzi et al. | |

OTHER PUBLICATIONS

The International Search report and the Written Opinion issued by KIPO on Aug. 31, 2012.

* cited by examiner

*Primary Examiner* — Necholus Ogden, Jr.
(74) *Attorney, Agent, or Firm* — Michael B. Fein; Eckert Seamans CHerin & Mellott, LLC

(57) ABSTRACT

An ethylene oxide-free, dioxane-free, and formaldehyde-free personal care concentrate composition free of ethoxylated components which is non-irritating to eyes comprising water, sodium alkyl sulfate, propanediol, and a synthetic amphoteric surfactant selected from the group consisting of cocamidopropyl hydroxysultaine and cocamidopropyl betaine is disclosed. This composition is especially suitable for baby shampoos which are not irritating. In some embodiments the composition is free of formaldehyde.

9 Claims, No Drawings

PERSONAL CLEANSING SYSTEMS EXHIBITING LOW EYE IRRITATION POTENTIAL

This application claims the benefit of U.S. Provisional Application Ser. No. 61/437,110, filed Jan. 28, 2011, herein incorporated by reference.

BACKGROUND OF THE INVENTION

This invention relates to personal cleaning compositions, more particularly to personal cleaning systems which have low eye irritation potential, sometimes called "no tears" or "tear free."

Current low eye irritation systems used in baby care applications typically contain one or more nonionic ethoxylated components such as sodium trideceth sulfate, PEG 150 distearate, or PEG 80 sorbitan laurate which can contribute potentially hazardous impurities, such as 1,4-dioxane and residual ethylene oxide to the finished formulations. Such typical compositions include as a principal component cocoamido propyl betaine as the amphoteric surfactant component, and also $C_{13}$ alkyl ether sulfate as anionic surfactant and PEG 150 distearate as nonionic thickener. Use of non-ethoxylated components is possible but often results in finished products which are substantially different from the current commercial formulations in physical properties and are generally more expensive and less preferred by consumers than the existing commercial systems containing ethoxylated surfactants.

It is an object of the invention to provide a personal cleaning system which has low eye irritation potential, has similar physical properties to state of the art personal cleaning commercial formulations, and is cost-effective.

SUMMARY OF THE INVENTION

This object and others which will become apparent from the following disclosure are achieved by the present invention which comprises in one aspect a personal cleansing system which is free of ethoxylated components. In some embodiments the composition is also free of nonionic surfactants, and polymeric materials, and therefore contains no residual ethylene oxide or dioxane, but is effective in consumer product applications such as baby care formulations which require low eye irritation, resulting in a clear, viscous, effective formulation which exhibits low irritation potential in standard eye irritation tests. In some embodiments the composition is also free of formaldehyde. While it is generally preferred to exclude polymeric components which cause irritation, in some embodiments a highly charged, highly water soluble cationic co-polymer that provides clarity and compatibility to anionic systems which is used in many hair and skin care applications such as Condicare PQ-7 can be used in conventional amounts. The composition of the invention is a low irritation personal care formulation which includes a low level of alkyl sulfates in combination with higher levels of sultaines and/or betaines as the base chassis modified with low levels of tertiary surfactants to adjust product attributes. We have discovered that while sultaines and betaines alone cause irritation in such formulations and alkyl sulfates alone cause irritation, together they impart reduced irritation in a synergistic manner.

In some embodiments the tertiary surfactants are one or more selected from the group consisting of decyl glucoside, sodium PCA, sodium cocoyl taurate, sodium cocoyl glycinate, disodium oleamido MIPA sulfosuccinate, disodium cocoamphodiacetate, disodium lauroamphodiacetate, cocamidopropyl hydroxysultaine.

The compositions can be made in either a ready-to use state by including fragrances, dyes, or other performance additives, such as anti-tangling polymers and preservatives, or manufactured in a more concentrated form which can be easily shipped and then diluted with water and converted into a specific finished consumer product as desired.

The compositions of the invention are economical, cost-effective cleansing systems free of potentially hazardous components which have similar physical properties and irritation profiles to systems based on ethoxylated ingredients which may have undesirable by-products and impurities present. The compositions can be made visually clear when let down.

DETAILED DESCRIPTION

The formulations of the invention are suitable for various personal care products such as shampoos, for example baby shampoos, pet products such as pet shampoos, and other personal care products used for sensitive skin.

The compositions comprise water and at least three other components, namely propylene glycol, sodium cocosulfate, and a sultaine or betaine. The amount of sultaine or betaine must be relatively large and the amount of sodium cocosulfate must be relatively small.

Other components are one or more surfactants selected from group consisting of disodium lauroamphodiacetate, disodium cocoamphodiacetate, lauroamphohydroxypropylesulfonate, and decyl glucoside, and one or more surfactants selected from the group consisting of disodium oleamido MIPA sulfosuccinate and disodium oleamido MEA sulfosuccinate.

The personal care products of the invention are prepared by letting down concentrates with water so that they are of a suitable viscosity. The concentrates are similar in solids % and pH to conventional personal care composition concentrates, usually at least 40% solids, and in some embodiments more than 45% solids. In some cases the solids levels are about 45-50%. The pH levels are about 6.5 to 9.5 for some embodiments, and for certain embodiments the pH is about 6.5 to 7.5.

The letdown viscosity is about 3000 to 4000 in some embodiments, with solids of about 10-12%. In some embodiments the letdown viscosity is 1100 to 4100, which is a steep response, and in other embodiments the letdown viscosity is about 2600-4600, which is a linear response.

EXAMPLES

The following examples illustrate a few non-limiting embodiments of the invention. All parts and percentages are by weight unless otherwise indicated.

Example 1

Ethylene Oxide-free Baby Shampoo

A let down composition having the components as charged and percentages as set forth in Table 1 was prepared from a concentrate.

TABLE 1

| COMPONENT | % BY WEIGHT (let down) | % BY WEIGHT (Concentrate) |
|---|---|---|
| DI Water | 76.18 | |
| Propanediol derived from vegetables | 1.3 | 5.5 |
| Sodium Cocosulfate (Mackol CAS-100N brand) | 1.4 | 6.0 |
| Disodium Lauroamphodiacetate (Mackam 2L brand) | 3.2 | 14 |
| Cocomidopropyl hydroxysultane ("CPS") (Mackam CBS 50G brand) | 13.6 | 59 |
| Disodium Oleamido MIPA Sulfosuccinate (Mackanate OPV-N brand) | 3.2 | 14 |

The concentrate composition set forth in Table 1 had 46-49% solids. A letdown was prepared by adding water to the concentrate to reduce the solids to 11-12%. The let down had a pH of 6.5-7, viscosity of about 3000 cps, and acceptable appearance for a baby shampoo. According to the industry-recognized irritation standard testing method known as HET CAM, this composition scored 0.11 which indicates non-irritating to eyes. The HET-CAM test followed protocol no. 47 of adapted from the one by Spielmann and Liebsch (INVITTOX 1992).

Example 2

Ethylene Oxide-free Baby Shampoo

A partial concentrate was prepared by charging the components set forth in Table 2 according to the percentages stated therein.

TABLE 2

| COMPONENT | % BY WEIGHT (Concentrate) |
|---|---|
| DI Water | 15.15 |
| Propanediol derived from vegetables | 5.5 |
| Sodium cocosulfate (Makol CAS-100N brand) | 6 |
| Disodium lauroamphodiacetate (Mackam 2L brand) | 14 |
| Cocamidopropylhydroxylsultaine ("CPS") (Mackam CBS 50G brand) | 59 |
| Sodium hydroxide, 50% | 0.35 |

The partial concentrate set forth in Table 2 had a pH (10%) of 9.5-11.0, viscosity of about 7500 cps max., solids (M) of 40-44%, and a clear liquid appearance. A let down was prepared by adding 3.2 parts of disodium sulfosuccinate olimido MIPA (Mackanate OPV-N brand) and sufficient water to form a finished product having a solids level of 11-12%.

According to the industry-recognized irritation standard testing method known as HET CAM, this composition scored 0.11 which indicates non-irritating to eyes. The HET-CAM test followed protocol no. 47 of adapted from the one by Spielmann and Liebsch (INVITTOX 1992).

Example 3

Baby Shampoo

A letdown formulation of a baby shampoo according to the invention was prepared by adding water to a concentrate, resulting in a composition having the components and concentrations set forth in Table 3. The properties of the composition are also set forth in Table 3.

TABLE 3

| Function | Component (% active ingredient) | Concentration |
|---|---|---|
| Solvent | Water | 88.0 to 91.0% |
| Polymer (detangling) | Polyquaternium-10 (>90%) | 0 to 0.1 |
| Chelating Agent | Tetrasodium EDTA (>95%) | 0 to 0.1 |
| Primary Surfactant | Sodium Coco Sulfate (>90%) | 1.5 to 1.8 |
| Tertiary Surfactant | Sodium PCA (~50%) | 0 to 4.0 |
| Tertiary Surfactant | Disodium Cocoamphoacetate (~38%) | 0 to 10.0 |
| Secondary Surfactant | Coco Betaine (~30%) | 0 to 18.0 |
| Secondary Surfactant | Cocamidopropyl betaine (~30%) | 0 to 18.0 |
| Tertiary Surfactant | Decyl Glucoside (~54% solids) | 0 to 3.5 |
| Tertiary Surfactant | Disodium Oleamido MIPA Sullfosuccinate (~38%) | 0 to 2.0 |
| Tertiary Surfactant | Sodium Cocoyl N-Methyltaurate (~34%) | 0 to 2.0 |
| Tertiary Surfactant | Sodium Cocoyl Glycinate (~30%) | 0 to 2.0 |
| Secondary Surfactant | Cocamidopropyl hydroxysultaine (~50%) | 0 to 16 |
| Tertiary Surfactant | Disodium lauroamphodiacetate (~38%) | 0 to 5.0 |
| Solvent | Vegetable sourced propylene glycol | 0 to 1.5 |
| Solvent | Glycerine | 0 to 1.5 |
| Preservative | Methylisothiazolinone (~9.5%) | 0 to 0.1 |
| Preservative | Potassium Sorbate (>90%) | 0 to 0.4 |
| Fragrance | Fragrance | 0 to 0.2 |
| pH Adjuster | Citric Acid | q.s. |

| Properties | |
|---|---|
| Typical % Non Volatile Matter | 9.0 to 12.0% |
| Typical pH (as-is) | 6.5 to 7.5 |
| Typical % NaCl | 0.3 to 1.3% |
| Typical viscosity cPs, RV5 10 rpm 1 min 25 deg C. | 1000 to 3000 |
| Typical Appearance @ 25 deg C. | Clear viscous liquid |

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. A personal care composition comprising water, sodium alkyl sulfate, a surfactant selected from the group consisting of disodium oleamido MIPA sulfosuccinate and disodium oleamido MEA sulfosuccinate, and a synthetic amphoteric surfactant, wherein the synthetic amphoteric surfactant is cocamidopropyl hydroxysultaine and the sodium alkyl sulfate is sodium cocosulfate, the composition being non-irritating to eyes and free of ethoxylated components.

2. The composition of claim 1 further comprising a surfactant selected from the group consisting of disodium lauroamphodiacetate, disodium cocoamphodiacetate, lauroamphohydroxypropylsulfonate, and decyl glucoside.

3. The composition of claim 1 in the form of a baby shampoo which is non-irritating to skin and eyes.

4. The composition of claim 1 wherein the composition is free of formaldehyde.

5. The composition of claim 1 wherein the composition is free of dioxane.

6. The composition of claim 1 wherein the composition is free of ethylene oxide.

7. The composition of claim 1 wherein the composition is free of nonionic surfactants and polymeric materials.

8. The composition of claim 1 in the form of a baby shampoo which is non-irritating to skin and eyes and is free of formaldehyde, ethylene oxide, non-ionic surfactants, and polymeric materials.

9. The personal care composition of claim 1 consisting of (a) water, (b) sodium cocosulfate, (c) a surfactant selected from the group consisting of disodium oleamido MIPA sulfosuccinate and disodium oleamido MEA sulfosuccinate, and (d) cocamidopropyl hydroxysultaine.

\* \* \* \* \*